United States Patent
DeGeorge et al.

(10) Patent No.: US 10,772,818 B2
(45) Date of Patent: Sep. 15, 2020

(54) METHODS AND KITS COMPRISING AN ANTIOXIDANT BOOSTER COMPOSITION FOR IMPROVING COLOR DURABILITY IN ARTIFICIALLY COLORED HAIR

(71) Applicant: L'OREAL, Paris (FR)

(72) Inventors: Michael DeGeorge, Old Bridge, NJ (US); Minnie Chan, San Diego, CA (US); Jim Singer, South Orange, NJ (US); Daniella Gonzalez-Toro, Hoboken, NJ (US); Jeffrey Wang, Jersey City, NJ (US); Lisa Jablonski, Edison, NJ (US); Martin Asare, Springfield, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/169,164

(22) Filed: Oct. 24, 2018

(65) Prior Publication Data

US 2019/0117549 A1 Apr. 25, 2019

Related U.S. Application Data

(60) Provisional application No. 62/576,241, filed on Oct. 24, 2017.

(51) Int. Cl.
*A61K 8/67* (2006.01)
*A61K 8/23* (2006.01)
(Continued)

(52) U.S. Cl.
CPC .............. *A61K 8/676* (2013.01); *A61K 8/22* (2013.01); *A61K 8/23* (2013.01); *A61K 8/411* (2013.01);
(Continued)

(58) Field of Classification Search
CPC ........ A61Q 5/10; A61K 8/411; A61K 8/4926; A61K 8/415; A61K 8/22; A61K 2800/882; A61K 2800/522
See application file for complete search history.

(56) References Cited

U.S. PATENT DOCUMENTS

| 5,804,172 A | 9/1998 | Ault |
| 6,106,579 A | 8/2000 | Kunz et al. |

(Continued)

FOREIGN PATENT DOCUMENTS

| DE | 19716780 C1 | 11/1998 |
| EP | 0943316 A2 | 9/1999 |
| WO | 2018053522 A1 | 3/2018 |

OTHER PUBLICATIONS

"Malibu Vegan Crystal Color Prep Gel Packet .17oz"; https://www.bewellstaywell.com/Malibu-Vegan-Crystal-Color-Prep-Gel-p/malibu1.htm.

(Continued)

*Primary Examiner* — Eisa B Elhilo
(74) *Attorney, Agent, or Firm* — Polsinelli PC

(57) ABSTRACT

The instant disclosure relates to methods and kits for artificially coloring hair and improving the durability of the artificially colored hair. The methods include: (I) combining an antioxidant booster composition, a hair coloring base composition, and a developer composition to form an antioxidant-enriched hair coloring composition within 2 hours of application to the hair; (II) applying the antioxidant enriched hair coloring composition to the hair and allowing the antioxidant enriched hair coloring composition to remain on the hair for a period of time; and (III) rinsing the antioxidant enriched hair coloring composition from the hair. The antioxidant booster composition can be included in a kit with a hair coloring base composition and/or a developer composition, wherein the antioxidant booster compo- (Continued)

sition, the coloring base composition, and the developer composition are separately contained.

21 Claims, 3 Drawing Sheets

(51) Int. Cl.
    *A61K 8/22*     (2006.01)
    *A61K 8/41*     (2006.01)
    *A61Q 5/10*     (2006.01)

(52) U.S. Cl.
    CPC .............. *A61K 8/415* (2013.01); *A61K 8/678* (2013.01); *A61Q 5/10* (2013.01); *A61K 2800/4324* (2013.01); *A61K 2800/522* (2013.01); *A61K 2800/882* (2013.01); *A61K 2800/884* (2013.01)

(56) References Cited

U.S. PATENT DOCUMENTS

| | | |
|---|---|---|
| 6,171,347 B1 | 1/2001 | Kunz et al. |
| 2004/0202622 A1 | 10/2004 | Quadir |
| 2004/0202623 A1 | 10/2004 | Quadir |
| 2006/0107470 A1 | 5/2006 | Audouset |
| 2006/0194333 A1 | 8/2006 | Pruche et al. |
| 2007/0044249 A1* | 3/2007 | Lisowski ........... A45D 19/0008 8/405 |
| 2009/0071494 A1 | 3/2009 | Nguyen et al. |
| 2011/0035885 A1* | 2/2011 | Zhang .................... A61K 8/494 8/406 |
| 2011/0203605 A1* | 8/2011 | Allard ...................... A61K 8/23 132/208 |
| 2011/0236334 A1* | 9/2011 | Jordan ................. A61K 8/8111 424/70.6 |
| 2018/0177690 A1 | 6/2018 | Boulineau et al. |

OTHER PUBLICATIONS

International Search Report and Written Opinion dated Feb. 1, 2019 for corresponding PCT Application No. PCT/US2018/057224.
Database GNPD; Mintel; "Hair Colourant", 2005 XP055543991
Database GNPD; Mintel; "Permanent Hair Dye", 2016 XP055544028
Third Party Observation submitted on Jan. 22, 2020.
Third Party Observation submitted on Jan. 23, 2020.

* cited by examiner

METHODS AND KITS COMPRISING AN ANTIOXIDANT BOOSTER COMPOSITION FOR IMPROVING COLOR DURABILITY IN ARTIFICIALLY COLORED HAIR

CROSS-REFERENCE TO RELATED APPLICATIONS

This application claims priority from Provisional Application No. 62/576,241, filed Oct. 24, 2017, which is incorporated herein by reference in its entirety.

FIELD OF THE DISCLOSURE

The present disclosure relates to methods and kits for improving color durability in artificially colored hair. Coloring fading is prevented or reduced and color intensity, quality, and vibrancy is maintained or extended.

BACKGROUND

Individuals often seek to change the color of their hair. Hair dyeing products for permanently altering the color of hair typically rely on a combination of compositions. For example, compositions containing oxidative dye precursors (also known as primary intermediates or oxidation bases) and compositions containing oxidizing agents such as peroxide and persulfate compounds.

Oxidative dye precursors are often colorless or weakly colored compounds, which, when combined with oxidizing agents, transition to provide colored species via a process of oxidative condensation. The shades obtained with oxidative dye precursors may be varied by combining them with one or more couplers. Couplers include, for example, aromatic meta-diamines, meta-aminophenols, meta-diphenols, and certain heterocyclic compounds, such as indole compounds.

The oxidizing agent(s) employed in permanent dyeing compositions may degrade the melanin of the hair, which, depending on the nature of the oxidizing agent, may lead to less pronounced lightening of the fibers. Thus, for relatively weak lightening, the at least one oxidizing agent may be, for example, hydrogen peroxide. When more substantial lightening is desired, peroxygenated salts, such as persulfates, may be used, usually in the presence of hydrogen peroxide.

Hair dyeing compositions typically contain an alkalizing agent such as aqueous ammonia. The alkalizing agents activate the oxidizing agent and also cause the hair shaft to swell, thus allowing the small oxidative dye precursor molecules to penetrate the cuticle and cortex before the oxidation condensation process is completed. The resulting larger-sized colored complexes from the oxidative reaction are then trapped inside the hair fiber, thereby permanently altering the color of the hair.

The duration for which dyed hair remains colored should be limited only by hair growth rate. As new hair grows from the roots of the hair, the natural color of the hair begins to appear. Unfortunately, the color (and the quality of the color) of the artificially colored hair tends to degrade over time. For example, repeated shampooing, combing and brushing, and exposure to sunlight, oxygen, and heat, can cause the color to fade. Red colors, for instance, are particularly susceptible to these degrading processes.

An underlying problem in achieving long-lasting color durability (fade resistance) is that only a portion of oxidative dye precursor molecules are able to penetrate the cuticle and cortex before the oxidation condensation process is completed. The more deeply the coloring molecules are able to penetrate the cuticle and cortex the more durable the color. Therefore, methods for improving the color durability of artificially colored hair, for example, by discovering or developing new methods that allow coloring molecules to more deeply penetrate and permanently adhere to the hair would be welcome.

SUMMARY OF THE DISCLOSURE

The present disclosure relates to artificially coloring hair and improving the resulting color durability (e.g., improving the fade resistance and the longevity of the color). The inventors discovered a surprising improvement in color quality and durability when an antioxidant booster composition is added to a coloring composition shortly before application of the coloring composition to the hair. Antioxidants have long been used in coloring compositions, especially in hair coloring base compositions, which include oxidative dye precursors and optionally couplers. Historically, the purpose for including the antioxidants is to extend the shelf-life of coloring base compositions by preventing the oxidative dye precursors from becoming oxidized prematurely. The oxidative dye precursors must be preserved so they are available to penetrate the cuticle and cortex where the oxidation condensation reaction should occur. As hair coloring base compositions age, a percentage of the antioxidants deteriorate over time; the antioxidants deteriorate as they perform their anti-oxidizing action of donating electrons to neutralize free radicals.

The inventors discovered that by enriching a coloring composition with antioxidants shortly before application of the coloring composition to the hair improves the color quality and durability of the color in the hair. While not wishing to be bound by any particular theory, the inventors suspect that the antioxidants added to the coloring composition function to prevent the oxidative dye precursors from reacting at the surface of the hair fibers. The antioxidants act to slow or prevent the oxidation condensation reaction from immediately occurring so that the oxidative dye precursors are able to more deeply penetrate the hair fibers. Once permanently lodged deep inside the hair fiber, the color is not easily removed. Therefore, the initial color quality and intensity that is achieved immediately upon artificially coloring the hair is maintained for longer periods of time.

The methods for coloring hair and improving the durability of the color include:
(I) combining an antioxidant booster composition with a hair coloring base composition and a developer composition to form an antioxidant-enriched hair coloring composition within about 2 hours of application to the hair;
(II) applying the antioxidant enriched hair coloring composition to the hair and allowing the antioxidant enriched hair coloring composition to remain on the hair for a period of time; and
(III) rinsing the antioxidant enriched hair coloring composition from the hair.

The antioxidant booster composition includes one or more antioxidants, and may also optionally include additional components such as fillers, carriers, conditioning agents, etc. Hair coloring base compositions include one or more oxidative dye precursors, and typically one or more alkalizing agents. Developer compositions include one or more oxidizing agents, usually in a cosmetically acceptable carrier.

Non-limiting examples of antioxidants that may be included in the antioxidant booster composition include ascorbic acid, sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and a mixture thereof. In some cases, ascorbic acid is particularly useful. Therefore, in some cases, the antioxidant booster composition includes at least ascorbic acid.

Many oxidative dye precursors are known and may be included in the hair coloring base compositions. Non-limiting examples of useful oxidative dye precursors include ortho- and/or para-aminophenols, ortho- and/or para-phenylenediamines, double bases, heterocyclic bases, acid addition salts thereof, and a mixture thereof.

Non-limiting examples of alkalizing agents that may be included in the hair coloring base compositions include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof.

Non-limiting examples of oxidizing agents that may be included in the developer composition include hydrogen peroxide, inorganic alkali metal peroxides (such as sodium periodate and sodium peroxide), organic peroxides (such as urea peroxide and melamine peroxide), inorganic perhydrate salts (such as the alkali metal salts of perborates, percarbonates, perphosphates, persilicates, persulfates), bromates, and a mixture thereof. In some cases, hydrogen peroxide is particularly useful.

The oxidizing agents of the developer composition are typically included with a cosmetically acceptable carrier. Non-limiting examples of appropriate carriers include water, water-soluble solvents, organic solvents, natural oils, synthetic oils, esters, hydrocarbons, silicones, and a mixture thereof. Water can be a particularly useful carrier and therefore in some cases, the developer composition includes at least water as one of the one or more carriers.

As discussed above, the methods of the instant disclosure include combining an antioxidant booster composition with a hair coloring composition shortly before applying the hair coloring composition to the hair. The multiple compositions used in the methods can therefore conveniently be provided in a kit. Kits according to the instant disclosure typically include: an antioxidant booster composition comprising one or more antioxidants, and optionally one or more fillers or carriers; and a hair coloring base composition comprising one or more alkalizing agents and one or more oxidative dye precursors; wherein the antioxidant booster composition and the hair coloring composition are separately contained. The kits may further include a developer composition, for example, a developer composition comprising one or more oxidizing agents and a cosmetically acceptable carrier.

Instructions, mixing components, brushes, gloves, measuring tools, etc., may also be included in the kits. The instruction can include mixing instructions and/or application instructions (e.g., instructions regarding how to dilute a concentrated neutralizing composition and/or instructions regarding how to use the compositions of the kits for coloring hair).

BRIEF DESCRIPTION OF THE DRAWINGS

Implementation of the present technology will now be described, by way of example only, with reference to the attached figures, wherein.

Figure 1:
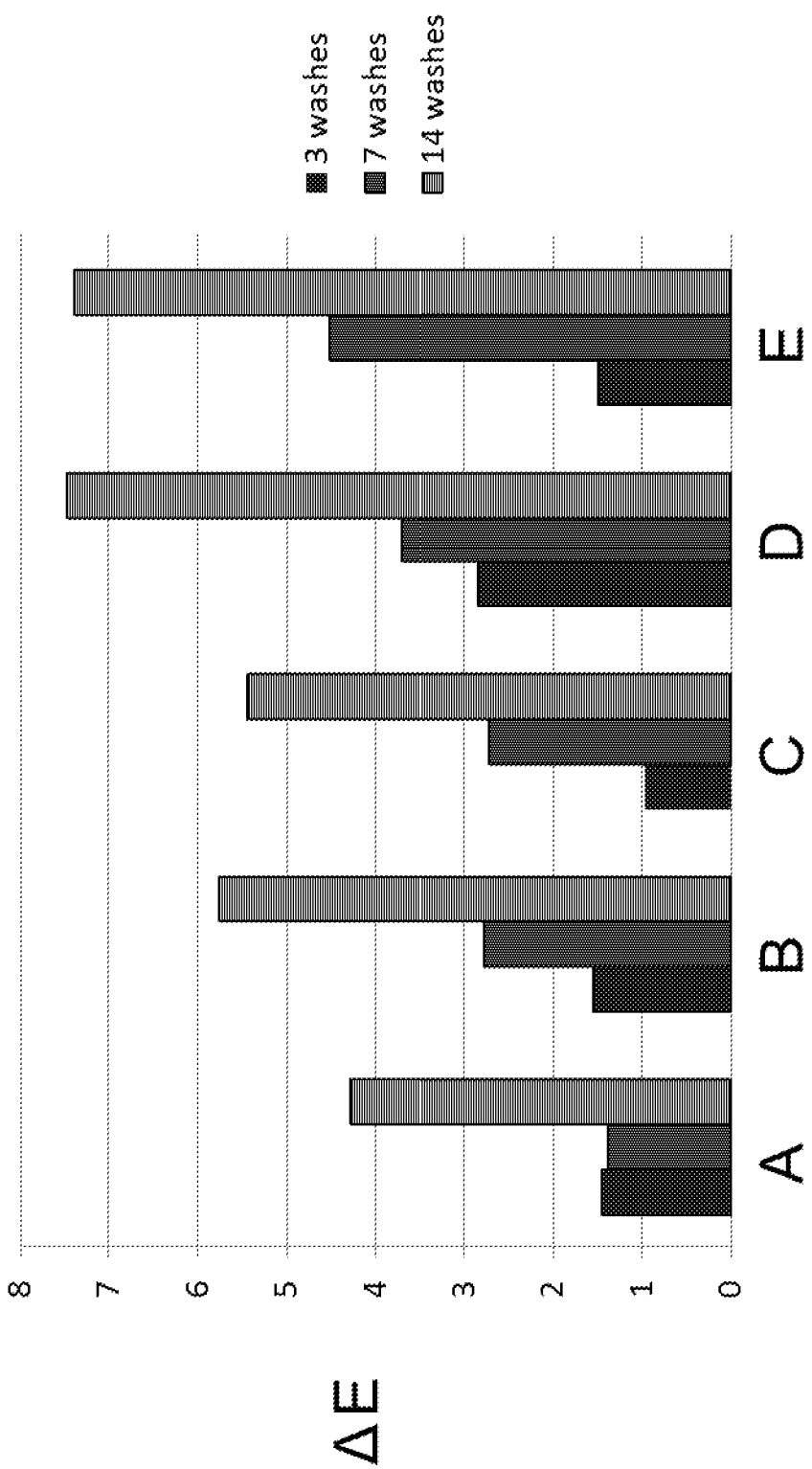
FIG. 1 is a graph showing the color fading of hair swatches treated with coloring compositions containing different amount of antioxidants added at the time of coloring.

It should be understood that the various aspects are not limited to the arrangements and instrumentality shown in the drawings.

DETAILED DESCRIPTION OF THE DISCLOSURE

The present disclosure relates to methods and kits for improving color durability in artificially colored hair using an antioxidant booster composition. The antioxidant booster composition is added to a hair coloring composition to create an antioxidant enriched hair coloring composition shortly before application to the hair. The antioxidant enriched hair coloring composition functions to allow oxidative dye precursor compounds to penetrate deep inside the cuticle and cortex of the hair fibers before the oxidation condensation process is completed. This results in the color deposition to be more durable (long-lasting)—the initial color intensity and vibrancy does not easily fade over time. The term "improving color durability" means that the longevity of the color imparted to the artificially colored hair is extended. In other words, color fading is reduced. It also means that the color intensity, quality, and vibrancy is maintained or extended for long periods of time. More specifically, the methods include:

(I) combining an antioxidant booster composition with a hair coloring base composition and a developer composition to form an antioxidant-enriched hair coloring composition within 2 hours of application to the hair;

(II) applying the antioxidant enriched hair coloring composition to the hair and allowing the antioxidant enriched hair coloring composition to remain on the hair for a period of time; and (III) rinsing the antioxidant enriched hair coloring composition from the hair.

The antioxidant booster composition includes one or more antioxidants, and may also optionally include one or more fillers or cosmetically acceptable carriers. Hair coloring base compositions include one or more oxidative dye precursors and typically one or more alkalizing agents. Developer compositions include one or more oxidizing agents, usually in a cosmetically acceptable carrier.

The antioxidant booster composition may be added directly to the hair coloring base composition before the hair coloring base composition is combined with the developer composition. However, adding the antioxidant booster composition after the hair coloring base composition and the developer composition have been mixed may be preferable. Mixing the hair coloring base composition and the developer composition before adding the antioxidant booster composition can help slow or prevent the antioxidants in the antioxidant booster composition from being destroyed by the one or more oxidizing agents in the developer composition. Accordingly, in some instances, the antioxidant booster composition is combined with the hair coloring base composition and the developer composition after the hair coloring base composition and the developer composition have already been combined with each another.

The hair coloring base composition, the developer composition, and the antioxidant booster composition are combined to create an antioxidant enriched hair coloring composition shortly before the antioxidant enriched hair coloring composition is applied to the hair. For example, the coloring base composition, developer composition, and the antioxidant booster composition are typically combined within about two hours of applying the combination (the antioxidant enriched hair coloring composition) to the hair. The hair coloring base composition, developer composition, and the antioxidant booster composition may be combined within about 2 hours, about 1.5 hours, about 1 hour, about 45 min., about 30 min., about 15 min., or about 5 min. of applying the combination the antioxidant enriched hair coloring composition) to the hair.

The antioxidant enriched hair coloring composition is applied to the hair and allowed to remain on the hair for a period of time, for example, a period of time sufficient for imparting a color change to the hair. The amount of time will vary depending on a variety of factors. Darker and coarser hair typically requires more time than lighter and softer hair. Other factors that influence the amount of time include the strength of the developer composition, the degree of color change desired, and the sensitivity of the individual's scalp to the chemicals in the antioxidant enriched hair coloring composition. In general, the antioxidant enriched hair coloring composition is allowed to remain on the hair for about 5 minutes to about 2 hours. In some instances, the antioxidant enriched hair coloring composition is allowed to remain on the hair from about 5 minutes to about 1.5 hours, about 5 minutes to about 1 hour, about 5 minutes to about 45 minutes, about 5 minutes to about 30 minutes, about 5 minutes to about 20 minutes, about 5 minutes to about 15 minutes, about 10 minutes to about 2 hours about 10 minutes to about 1.5 hours, about 10 minutes to about 1 hour, about 10 minutes to about 45 minutes, or about 10 minutes to about 30 minutes. After the antioxidant enriched hair coloring composition is allowed to remain on the hair for a period of time, it is typically rinsed from the hair with water. Upon rinsing, the hair may also be shampooed and/or conditioned with a shampoo and/or conditioner.

The antioxidant booster composition includes one or more antioxidants and optionally one or more fillers, carriers, and/or conditioning agents. Many antioxidants that are used in hair coloring base compositions may be useful in the antioxidant booster compositions of the instant disclosure. For example, non-limiting examples of antioxidants include ascorbic acid, sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and a mixture thereof. The selection of appropriate antioxidant(s) useful in a particular antioxidant booster composition may depend on a variety of factors, for example, the type of oxidative dye precursors of the hair coloring base composition, the types of optional couplers that may be present in the hair coloring base composition, etc. In some instances, the antioxidant booster composition includes ascorbic acid, sodium sulfite, sodium metabisulfite, or a mixture thereof. A more exhaustive but non-limiting list of antioxidants that may be included in the antioxidant booster composition is provided later, under the heading "Antioxidants."

The antioxidant booster composition may include only antioxidant(s), or it may include additional components such as fillers, carriers, and/or conditioning agents. The fillers and/or carriers may vary depending on whether the antioxidant booster composition is liquid or solid (e.g., powder). The fillers and/or carriers may be compounds that will not react with the antioxidants and will not negatively impact the active compounds in the hair coloring base composition and/or the developer composition. In other words, the fillers and/or carriers are compounds that are cosmetically acceptable and are not detrimental to the antioxidants in the antioxidant booster composition or to the active compounds in the hair coloring base composition and developer composition (e.g., alkalizing agents, oxidizing agents, oxidative dye precursors, etc.).

Non-limiting examples of fillers include starches, maltodextrins, calcium silicates, perlites, zeolites, polylactic acids, silicas, polyamide powders, polyvinylpyrrolidones, dextrose, oligosaccharides, celluloses, diatomite, diatomaceous earth, talc, clays, silicon dioxide, magnesium silicates (i.e. talc powder), clays, vitamin powders (such as vitamin B3—niacin) amino acid powders and their derivatives, and a mixture thereof. Fillers are particularly useful when the antioxidant booster composition is in a solid/powder form.

Non-limiting examples of carriers include water, organic solvents, natural oils, synthetic oils, esters, hydrocarbons, silicones, and a mixture thereof. In particular, exemplary carriers include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins, and a mixture thereof. Carriers are particularly useful when the antioxidant booster composition is in a liquid form.

If a filler and/or carrier is included in the antioxidant booster composition, it may be present in an amount that varies widely. For example, one or more fillers and/or one or more carriers may be present in an amount of about 1 to about 99 wt. %, based on the total weight of the antioxidant booster composition. In some cases, the total amount of the one or more fillers and/or the one or more carriers is about 1 to about 80 wt. %, about 1 to about 70 wt. %, about 1 to about 60 wt. %, about 1 to about 50 wt. %, about 1 to about 40 wt. %, about 5 to about 70 wt. %, about 5 to about 60 wt. %, about 5 to about 50 wt. %, about 5 to about 40 wt. %, about 10 to about 70 wt. %, about 10 to about 60 wt. %, about 10 to about 50 wt. %, or about 10 to about 40 wt. %, based on the total weight of the antioxidant booster composition. In some instances, the total amount of antioxidant(s) is at least 50 wt. %, based on the total weight of the antioxidant booster compositions. In such cases, the total amount of the one or more fillers and/or one or more carriers is about 1 to about 50 wt. %, about 2 to about 50 wt. %, about 5 to about 50 wt. %, about 10 to about 50 wt. %, about 1 to about 40 wt. %, about 2 to about 40 wt. %, about 5 to about 40 wt. %, or about 10 to about 40 wt. %, based on the total weight of the antioxidant booster composition.

Conditioning agents may also optionally be included in the antioxidant booster compositions. The one or more conditioning agent may include: A) amphoteric conditioning agents, (B) cationic conditioning agents, (C) non-ionic conditioning agents, and (D) anionic conditioning agents. Examples of each type are listed below.

(A) Amphoteric conditioning agents: arginine, asparagines, aspartic acid, glycine, glutamic acid, lysine, methionine, phenylalanine, serine, threonine, tyrosine, tryptophan, valine, gelatin, Quaternium-27, oleamidopropyl betaine, disodium cocoamphodiacetate, disodium cocoamphodipropionate, disodium lauroamphodiacetate, sodium cocoamphopropionate, sodium cocoamphoacetate, meadowfoam delta lactone, cocoamidopropyl betaine, cocoamidopropyl hydroxysultaine, lauramidopropyl betaine, carnitine, hydroxyproline, acetyl hydroxy proline, isoleucine, lauroyl lysine, lauroyl sarcosine, polylysine, proline, rice amino acids, silk amino acids, wheat amino acids and mixture thereof;

(B) Cationic conditioning agents: hydroxypropyltrimonium chloride, cocotrimonium methosulfate, olealkonium chloride, steartrimonium chloride, babassuamidopropalkonium chloride, brassicamidopropyl dimethylamine, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, dilinoleamidopropyl dimethylamine dimethicone PEG-7 phosphate and mixture thereof;

(C) Non-ionic conditioning agents: petrolatum, mineral oil, lanolin oil, *cocas nucifera* (coconut) oil, *Olea Europea* (Olive) fruit oil, *Simmondsia Chinensis* (Jojoba) seed oil, *Prunus Armeniaca* (Apricot) kernel oil, *Crambe Abyssinica* seed oil, vegetable oil, *Zea Mays* (Corn) oil, caprylyl glycol, cetyl glycol, glycerin, sarcosine, hydroxypropyl guar, cocamide MIPA, cyclomethicone, dimethicone, $C_{26-28}$ alkyl dimethicone, Polysilicone-13, acetylated lanolin alcohol, cetearyl isononanoate, cetearyl ethylhexanoate, Triethylhexanoin, phytantriol, PPG-5 Butyl Ether, coco-betaine, acetamide MEA, behenamide MEA, linoleamide DEA, linolenic acid, maltodextrin, squalane, squalene, *Salix Alba* (Willow) bark extract, *Morus Alba* (Mulberry) leaf, phenyltrimethicone, hexyl dimethicone, capric/caprylic triglyceride, cetearyl palmitate, hydrogenated olive oil hexyl esters, *Ginkgo Biloba* nut extract, inositol, Dimethicone Beeswax, PEG-8 dimethicone, PPG-12 dimethicone, panthenol, methanediol, ceramide 3, Phytosphingosine, salicylic acid, linoleamide MEA, linoleamide MIPA, niacin, thiodiglycoamide, hydrolyzed soy protein, hydrolyzed oat protein, hydrolyzed rice protein, hydrolyzed vegetable protein, hydrolyzed yeast protein, casein, collagen, procollagen, keratin, glycoproteins, hydrolyzed wheat protein and mixture thereof; and (D) Anionic conditioning agents: sodium glutamate, potassium cocoyl glutamate, cocoyl sarcosine, histidine, sodium lauroyl glutamate, stearoyl sarcosine, whey protein, methyl cocoate, sodium cocoate, linoleic acid and mixture thereof.

In some instances, cationic conditioning polymers may be useful. Non-limiting exmamples of cationic conditioning polymers include Suitable cationic conditioning polymers include, for example: copolymers of 1-vinyl-2-pyrrolidone and 1-vinyl-3-methylimidazolium salt (e.g., chloride salt) (Polyquaternium-16); copolymers of 1-vinyl-2-pyrrolidone and dimethylaminoethyl methacrylate (Polyquaternium-11); cationic diallyl quaternary ammonium-containing polymers, including, for example, dimethyldiallylammonium chloride homopolymer and copolymers of acrylamide and dimethyldiallylammonium chloride (Polyquaternium 6 and Polyquaternium 7); polymethacrylamidopropyl trimonium chloride; and Polyquaternium-37.

Additional suitable cationic conditioning polymers include cationic cellulose derivatives. Cationic cellulose derivative useful herein include, for example, salts of hydroxyethyl cellulose reacted with trimethyl ammonium substituted epoxide (Polyquaternium 10); and Polyquaternium-4 Cationic guar polymers, such as guar hydroxypropyltrimonium chloride may also be used.

In instances where the antioxidant booster composition is in a powder form, the antioxidant booster composition may optionally include one or more powdered conditioning agents. Non-limiting examples include dimethyldiallylammonium chloride acrylic acid polymer (polyquaternium-22), methyacryloylox-ethyl trimethyl ammonium methylsulfate (METAMS) and acrylamide (ACAM) (MERQUAT 5), polyvinylpyrrolidone (PVP), poly(vinyl acetate) (PVA), and a mixture thereof.

Hair coloring base compositions include one or more oxidative dye precursors, which may also be referred to as "primary intermediates" or "oxidation bases." Oxidative dye precursors are often colorless or weakly colored compounds, which, when combined with oxidizing products, reactive via oxidative condensation to provide colored species. Non-limiting examples of oxidative dye precursors include aromatic diamines, polyhydric phenols, amino phenols, and derivatives of these compounds, such as, for example, N-substituted derivatives of the amines, and ethers of the phenols, ortho- or para-aminophenols, ortho- or para-phenylenediamines, double bases, heterocyclic bases, and the acid addition salts thereof. A more exhaustive but non-limiting list of oxidative dye precursors that may be included in the hair coloring base compositions is provided later, under the heading "Oxidative Dye Precursors."

The shades obtained with oxidative dye precursors may often be varied by combining them with at least one coupler. Non-limiting examples of couplers include aromatic meta-diamines, meta-aminophenols, meta-diphenols, and certain heterocyclic compounds, such as indole compounds. A more exhaustive but non-limiting list of couplers that may be included in the hair coloring base compositions is provided later, under the heading "Couplers." The variety of molecules used as oxidative dye precursors and couplers allow for a wide range of colors to be obtained. Moreover, the hair coloring base composition may additionally include one or more direct dyes, pigments, and mixtures thereof.

The total amount of the one or more oxidative dye precursors may vary but in some cases is often about 0.0001 to about 15 wt. %, based on the total weight of the hair coloring base composition. In some instances, the total amount of the one or oxidative dye precursors is about 0.0001 to about 12 wt. %, about 0.0001 to about 10 wt. %, about 0.0001 to about 8 wt. %, about 0.0001 to about 5 wt. %, about 0.001 to about 12 wt. %, about 0.001 to about 10 wt. %, about 0.001 to about 8 wt. %, about 0.001 to about 5 wt. %, about 0.005 to about 10 wt. %, about 0.005 to about 8 wt. %, about 0.005 to about 6 wt. %, or about 0.005 to about 5 wt. %, based on the total weight of the hair coloring base composition.

The total amount of couplers that may be included in the hair coloring base compositions may also vary, but in general, the total amount of the one or more couplers may be about 0.0001 to about 15 wt. %, based on the total weight of the hair coloring base composition. In some instances, the total amount of the one or couplers is about 0.0001 to about 12 wt. %, about 0.0001 to about 10 wt. %, about 0.0001 to about 8 wt. %, about 0.0001 to about 5 wt. %, about 0.001 to about 12 wt. %, about 0.001 to about 10 wt. %, about 0.001 to about 8 wt. %, about 0.001 to about 5 wt. %, about 0.005 to about 10 wt. %, about 0.005 to about 8 wt. %, about 0.005 to about 6 wt. %, or about 0.005 to about 5 wt. %, based on the total weight of the hair coloring base composition.

The hair coloring base compositions often include one or more alkalizing agents. The alkalizing agents can have multiples roles in the coloring process. For instance, the alkalizing agent typically causes the hair shaft to swell, thus allowing the small oxidative dye precursor molecules to more easily penetrate the cuticle and cortex. Also, the alkalize agent can activate the oxidizing agent(s) of the developer composition and contribute to the oxidation condensation process. Non-limiting examples of alkalizing agents include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof. In some cases, alkalizing agents such as ammonia and/or alkanolamines are particularly useful, for example, ammonia and/or monoethanolamine.

The total amount of alkalizing agent(s) in the hair coloring base composition can vary but in some cases may be about 0.1 to about 40 wt. %, based on the total weight of the hair coloring base composition. In some cases, the total amount of the one or more alkalizing agents is about 0.1 to about 30 wt. %, about 0.1 to about 25 wt. %, about 0.1 to about 20 wt. %, about 0.1 to about 15 wt. %, about 0.1 to about 10 wt. %, or about 0.5 to about 10 wt. %, based on the total weight of the hair coloring base composition.

The hair coloring base composition may include additional components such as, for example, one or more fatty compounds, water-soluble solvents, thickening agents, surfactants, antioxidants, etc.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. A more exhaustive but non-limiting list of fatty compounds that may be included in the hair coloring base compositions is provided later, under the heading "Fatty Compounds."

The total amount of the one or more fatty compounds may vary but, if present, it typically about 1 to about 50 wt. %, based on the total weight of the hair coloring base composition. The total amount of the one or more fatty compounds may be about 1 to about 40 wt. %, about 1 to about 30 wt. %, about 1 to about 20 wt. %, about 5 to about 50 wt. %, about 5 to about 40 wt. %, about 5 to about 30 wt. %, about 5 to about 20 wt. %, about 10 to about 50 wt. %, about 10 to about 40 wt. %, or about 10 to about 30 wt. %, based on the total weight of the hair coloring base composition.

Water-soluble solvents may be included in the hair coloring base composition. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, $C_{1-4}$ alcohols, organic solvents, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, ethanol, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the one or more water-soluble solvents can vary but is typically about 1 to about 50 wt. %, based on the total weight of the hair coloring base composition. In some cases, the total amount of the one or more water-soluble solvents is about 1 to about 40 wt. %, about 1 to about 30 wt. %, about 1 to about 20 wt. %, about 5 to about 50 wt. %, about 5 to about 40 wt. %, about 5 to about 30 wt. %, or about 5 to about 25 wt. %, based on the total weight of the hair coloring base composition.

One or more thickening agents may also be included in the hair coloring base composition. Non-limiting examples of thickening agents include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxylpropyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, acrylates copolymer, polyethyleneimine, bentonite, aluminum magnesium silicate, laponite, hectonite, anhydrous silicic acid, and a mixture thereof. In some cases, the one or more thickening agents are selected from the group consisting of cross linked acrylic acid polymers (carbomer), methyl cellulose, ethyl cellulose, hydroxyethyl cellulose, hydroxypropyl methyl cellulose, hydroxylpropyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof.

The total amount of the one or more thickening agents can vary but is typically about 0.01 to about 10 wt. %, 0.05 to about 5 wt. %, or about 0.1 to about 4 wt. %, based on the total weight of the hair coloring base composition. The total amount of the one or more thickening agents may be about 0.01 to about 8 wt. %, about 0.01 to about 5 wt. %, about 0.1 to about 8 wt. %, about 0.1 to about 5 wt. %, about 0.5 to about 8 wt. %, or about 0.5 to about 5 wt. %, based on the total weight of the hair coloring base composition.

The hair coloring base composition may include water. For example, the hair coloring base composition may include about 1 to 80 wt. % water, based on the total weight of the hair coloring base composition. The total amount of water may be about 5 to about 80 wt. %, about 10 to about 80 wt. %, about 20 to about 80 wt. %, about 30 to about 80 wt. %, or about 40 to about 80 wt. %, based on the total weight of the hair coloring base composition.

The hair coloring base composition may include antioxidants, such as the antioxidants recited for inclusion in the antioxidant booster composition. Antioxidants formulated into a hair coloring base composition function to preserve the integrity of the hair coloring base composition and the oxidative dye precursors of the hair coloring base composition. The total amount of the one or more antioxidants may vary but is typically about 0.01 to about 8 wt. %, about 0.1 to about 6 wt. %, about 0.1 to about 5 wt. %, or about 0.5 to about 5 wt. %, based on the total weight of the hair coloring base composition.

The hair coloring base composition may be in a variety of different forms including, for example, a liquid, a lotion, a gel, a paste, a cream, etc. In some cases the hair coloring base composition is an emulsion such as, for example, a liquid emulsion or a liquid-cream emulsion.

In one embodiment, the hair coloring base compositions of may include:
(i) about 0.1 to about 25 wt. %, about 0.1 to about 15 wt. %, or about 0.5 to about 10 wt. % of one or more oxidative dye precursors, for example, one or more N-substituted derivatives of the amines, and ethers of the phenols, ortho- or para-aminophenols, ortho- or para-phenylenediamines, double bases, heterocyclic bases, and the acid addition salts thereof;
(ii) about 0.1 to about 20 wt. %, about 0.1 to about 15 wt. %, or about 0.5 to about 10 wt. %, of one or more alkalizing agents, for example, ammonium, ammonium compounds (e.g., ammonium hydroxide, ammonium carbonate, ammonium chloride, ammonium sulfate, ammonium nitrate, ammonium phosphate, ammonium acetate, ammonium hydrogen carbonate, ammonium carbamate), percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof;
(iii) about 0.0001 to about 12 wt. %, about 0.0001 to about 10 wt. %, or about 0.0001 to about 8 wt. % of one or more couplers, for example, aromatic meta-diamines, meta-aminophenols, meta-diphenols, heterocyclic compounds (indole compounds), and a mixture thereof;
(iv) optionally, about 1 to about 50 wt. %, about 1 to about 40 wt. %, or about 5 to about 10 wt. %, of one or more fatty compounds, for example, one or more oils;
(v) optionally, about 1 to about 50 wt. %, about 1 to about 30 wt. %, or about 1 to about 25 wt. % of one or more water-soluble compounds, for example, glycerin, $C_{1-4}$ alcohols, organic solvents, polyols, glycols, and a mixture thereof;
(vi) optionally, about 0.1 to about 10 wt. %, about 0.1 to about 8 wt. %, or about 0.5 to about 6 wt. % of one or more thickening agents; and
(vii) water.

The developer composition includes one or more oxidizing agents present in an amount sufficient to develop a color when mixed with a hair coloring base composition. Non-limiting examples of oxidizing agents include hydrogen peroxide, inorganic alkali metal peroxides (such as sodium periodate and sodium peroxide), organic peroxides (such as urea peroxide and melamine peroxide), inorganic perhydrate salts (such as the alkali metal salts of perborates, percarbonates, perphosphates, persilicates, persulfates), bromates, and a mixture thereof. In some cases, the developer composition includes hydrogen peroxide.

The total amount of the one or more oxidizing agents in the developer composition may vary, but is typically about 0.5 to about 50 wt. %, based on the total weight of the developer composition. In some instances, the total amount of the one or more oxidizing agents is about 0.5 to about 40 wt. %, about 1 to about 50 wt. %, about 1 to about 40 wt. %, about 1 to about 30 wt. %, about 1 to about 20 wt. %, about 5 to about 50 wt. %, about 5 to about 40 wt. %, about 5 to about 30 wt. %, or about 5 to about 20 wt. %, based on the total weight of the developer composition.

The developer composition may be in the form of a powder, gel, liquid, foam, lotion, cream, mousse, or emulsion. Additionally, the developer composition may be anhydrous. The term "anhydrous" means that the developer composition is either completely free of water or contains no appreciable amount of water, preferably no more than 1% by weight, and more preferably no more than 0.5% by weight, based on the weight of the developer composition.

The developer composition may include one or more cosmetically acceptable carriers such as, for example, water, water-soluble solvents, organic solvents, natural oils, synthetic oils, esters, hydrocarbons, silicones, and a mixture thereof. When the developer composition is anhydrous, the one or more solvent may be organic solvents. Non-limiting examples of organic solvents include ethanol, isopropyl alcohol, benzyl alcohol, phenyl ethyl alcohol, glycols and glycol ethers, such as ethylene glycol, propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum, isoparaffins, and mixtures thereof.

The total amount of the one or more cosmetically acceptable carriers in the developer composition may vary, but in some cases is from about 0.5 to 70 wt. %, based on the total weight of the developer composition. The total amount of the one or more cosmetically acceptable carriers may be about 1 to about 70 wt. %, about 20 to about 60 wt. %, or about 5 to about 50 wt. %, based on the total weight of the developer composition.

The hair coloring base composition and the developer composition can be mixed at a ratio of about 1:5 to about 5:1 (hair coloring base composition: developer). In some cases, the ratio is about 1:3 to about 3:1, about 1:2 to about 2:1, about 1:1 to about 5:1, about 1:1 to about 3:1, about 1:1 to about 2:1, about 5:1 to about 1:1, about 3:1 to about 1:1, or about 2:1 to about 1:1 (hair coloring base composition: developer).

The amount of the antioxidant booster composition that is combined with the hair coloring base composition and the developer composition will vary depending on the concentration of antioxidants in the antioxidant booster composition. If the concentration of antioxidants is high in the antioxidant booster composition, less antioxidant booster composition will be needed.

In some instances, the antioxidant booster composition is added so that the total amount of the one or more antioxidants in the antioxidant enriched hair coloring composition is about 0.001 to about 5 wt. %, based on the total weight of the enriched antioxidant booster composition. In some cases, the antioxidant booster composition is added so that the total amount of the one or more antioxidants in the antioxidant enriched hair coloring composition is about 0.001 to about 4 wt. %, about 0.001 to about 3 wt. %, about 0.001 to about 2 wt. %, about 0.001 to about 1 wt. %, about 0.001 to about 0.5 wt. %, about 0.01 to about 4 wt. %, about 0.01 to about 3 wt. %, about 0.01 to about 3 wt. %, about 0.01 to about 2 wt. %, about 0.01 to about 1 wt. %, about 0.01 to about 0.5 wt. %, about 0.1 to about 4 wt. %, about 0.1 to about 3 wt. %, about 0.1 to about 2 wt. %, about 0.1 to about 1 wt. %, or about 0.1 to about 0.5 wt. %, based on the total weight of the antioxidant enriched booster composition.

Surfactants can be useful in one or both of the hair coloring base compositions and the developer composition. The one or more surfactants may be anionic, amphoteric, non-ionic, zwitterionic, cationic surfactants, and mixtures thereof.

Non-limiting examples of surfactants alkyl sulfates, alkyl ether sulfates, alkylamino ether sulfates, alkylarylpolyether sulfates, monoglyceride sulfates; alkyl sulphonates, alkyl phosphates, alkyl amide sulphonates, alkyl aryl sulphonates, .alpha.-olefin sulphonates, paraffin sulphonates; $(C_6-C_{24})$ alkyl sulphosuccinates, $(C_6-C_{24})$alkyl ether sulphosuccinates, $(C_6-C_{24})$alkyl amide sulphosuccinates; $(C_6-C_{24})$alkyl sulphoacetates; $(C_6-C_{24})$acryl sarcosinates; and $(C_6-C_{24})$ acryl glutamates; and salts of these compounds (for example, alkali metal salts, such as sodium salts, ammonium salts, amine salts, amino alcohol salts and magnesium salts).

Anionic surfactants may be for example, $(C_6-C_{24})$alkylpolyglycoside carboxylic esters, such as alkylglucoside citrates, alkylpolyglycoside tartrates and alkylpolyglycoside sulphosuccinates, alkylsulphosuccinamates; acylisethionates and N-acyl taurates, alkyl radicals and acyl radicals of these different compounds, such as those comprising from 12 to 20 carbon atoms, and at least one aryl radical may be chosen, for example, from phenyl and benzyl groups. At least one anionic surfactant may be chosen, for example, from fatty acid salts, such as oleic, ricinoleic, palmitic and stearic acid salts, coconut oil acid and hydrogenated coconut oil acid; acyl lactylates wherein the acyl radical comprises 8 to 20 carbon atoms. At least one anionic surfactant may be chosen, for example, from alkyl D-galactoside uronic acids and their salts, polyoxyalkylenated $(C_6-C_{24})$alkyl ether carboxylic acids, polyoxyalkylenated $(C_6-C_{24})$alkyl aryl ether carboxylic acids, polyoxyalkylenated $(C_6-C_{24})$alkylamido ether carboxylic acids and their salts, for example, those comprising from 2 to 50 alkylene oxide groups, such as ethylene oxide groups, and mixtures thereof.

Non-limiting examples of nonionic surfactants include polyethoxylated and/or polypropoxylated alkyl phenols, alpha-diols and alcohols, comprising fatty chains comprising, for example, from 8 to 18 carbon atoms, and the number of ethylene oxide and/or propylene oxide groups may range from 2 to 50. The at least one non-ionic surfactant may be chosen, for example, from copolymers of ethylene oxide and of propylene oxide, condensates of ethylene oxide and/or of propylene oxide with fatty alcohols; polyethoxylated fatty amides comprising, for example, from 2 to 30 mol of ethylene oxide, polyglycerolated fatty amides comprising on average 1 to 5, and, for example, 1.5 to 4, glycerol groups; polyethoxylated fatty amines comprising, for example, from 2 to 30 mol of ethylene oxide; oxyethylenated fatty acid esters of sorbitan comprising, for example, from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$ alkyl amine oxides and N-acylaminopropylmorpholine oxides.

Non-limiting examples of amphoteric or zwitterionic surfactants include aliphatic secondary and tertiary amine derivatives wherein the aliphatic radical comprises linear and branched chains comprising 8 to 18 carbon atoms and comprising at least one water-solubilizing anionic group (for example, carboxylate, sulphonate, sulfate, phosphate and phosphonate); and $(C_8-C_{20})$alkylbetaines, sulphobetaines, $(C_8-C_{20})$alkylamido$(C_1-C_8)$alkylbetaines and $(C_8-C_{20})$alkylamido$(C_1-C_8)$alkylsulphobetaines.

Non-limiting examples of cationic surfactants include salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

The total amount of the one or more surfactants that may be present in the hair coloring base composition and/or the developer composition will vary, but can be about 0.01 to about 30 wt. %, based on the total weight of the composition (the total weight of the hair coloring base composition or the total weight of the developer). In some cases, the total amount of the one or more surfactants is about 0.01 to about 20 wt. %, about 0.01 to about 15 wt. %, about 0.01 to about 10 wt. %, about 0.1 to about 30 wt. %, about 0.1 to about 20 wt. %, about 0.1 to about 15 wt. %, about 0.1 to about 10 wt. %, or about 0.1 to about 5 wt. %.

The multiple compositions used in the methods discussed above can conveniently be provided in a kit. Kits according to the instant disclosure typically include: an antioxidant booster composition comprising one or more antioxidants, and optionally one or more fillers or carriers; and a hair coloring base composition comprising one or more alkalizing agents and one or more oxidative dye precursors; wherein the antioxidant booster composition and the hair coloring composition are separately contained. The kits may further include a developer composition, for example, a developer composition comprising one or more oxidizing agents and a cosmetically acceptable carrier.

Instructions, mixing components, brushes, gloves, measuring tools, etc., may also be included in the kits. The instruction can include mixing instructions and/or application instructions (e.g., instructions regarding how to dilute a concentrated neutralizing composition and/or instructions regarding how to use the compositions of the kits for coloring hair).

More exhaustive but non-limiting lists of components useful in the antioxidants compositions of the instant disclosure are provided below.

Antioxidants

Many antioxidants that are useful in hair coloring base compositions. For example, non-limiting examples of antioxidants include ascorbic acid, sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and a mixture thereof. The selection of appropriate antioxidant(s) useful in a particular antioxidant booster composition may depend on a variety of factors, for example, the type of oxidative dye precursors of the hair coloring base composition, the types of optional couplers that may be present in the hair coloring base composition, etc. In some instances, the antioxidant booster composition includes ascorbic acid, sodium sulfite, sodium metabisulfite, or a mixture thereof.

The antioxidants may include flavonoids. Flavonoids exhibit chelating properties with metal ions and may reduce the oxidative damage from metal ions by sequestering the ions. Formation and stability of flavonoids-metal-chelates is a structure-dependent function. Flavonoids with a catechol moiety and with hydrogen bonds between hydroxyl group in the 5- and 3-positions have chelating properties.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, emblica officinalis, and bioflavonoids from rose hip and citrus may be used including watersoluble bioflavonoids such as hesperidin methyl chalcone may also be used.

Other antioxidants, which may be incorporated, include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E and other carotenoids.

The flavonoid may be a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals. The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C., and synthetic Safalcone.

Oxidation Dye Precursors

The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-I, N,N'-bis(.beta.-hydroxyethyl)-N,N'-bis(4'-aminophenypethylenediamine, N,N'-bis(4-aminophenyl)tetramethylenediamine, N,N'-bis(.beta.-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethypamino] ethanol, 2-[(3-aminopyrazolo[1,5-a]pyrid-7-yl)(2-hydroxyethypamino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a] pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H, 5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H, 5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1, 2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H, 5H-pyrazolo[1,2-a]pyrazol-1-one and/or a salt thereof will preferentially be used as heterocyclic bases.

Couplers

The couplers include those conventionally used in oxidative methods of coloring hair, for example, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d] oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the following general formula:

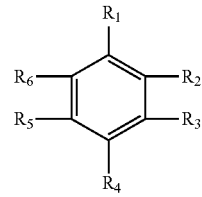

wherein $R_1$ is unsubstituted hydroxy or amino, or hydroxy or amino substituted with one or more $C_{1-6}$ hydroxyalkyl groups, $R_3$ and $R_6$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethy)paminoppenzene], 1-methoxy-2-amino-4-[(beta-hydroxyethyl)amino]benzene, 1-hydroxy-3-(dimethylamino)benzene, 6-methyl-1-hydroxy-3[(beta-hydroxyethypamino]penzene, 2,4-dichloro-1-hydroxy-3-aminobenzene, 1-hydroxy-3-(diethylamino) benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl) amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy- N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methyl pyrazolo[1,5-a]-benzimidazole, and the acid addition salts thereof.

In one embodiment, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and mixtures thereof.

In general, the acid addition salts of the oxidation bases and couplers may be chosen from hydrochlorides, hydrobromides, sulfates, tartrates, lactates, and acetates.

Fatty Compounds

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isononanoate isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

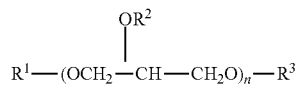

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substitued fatty acids, and a mixture thereof. Nonlimiting examples of fatty acid derivatives inlcude ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher metling point fatty compounds may also be used, for example, fatty compounds having a metling point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Thickening Agents

Thickening agents (also referred to as thickeners, rheology modifying agents, or viscosity modifying agents) are well known. Classes of such agents include, but are not limited to, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition.

Implementation of the present disclosure is provided by way of the following examples. The examples serve to illustrate the technology without being limiting in nature.

EXAMPLE 1

Antioxidant Booster Compositions

| Function | INCI US Name | WT. % |
| --- | --- | --- |
| Antioxidant Booster Composition A ||| 
| Antioxidant | Ascorbic Acid | 50 |
| Antioxidant | Sodium Sulfite | 50 |
| TOTAL | | 100 |
| Antioxidant Booster Composition B ||| 
| Antioxidant | Ascorbic Acid | 70 |
| Filler | Corn Starch | 30 |
| TOTAL | | 100 |
| Antioxidant Booster Composition C ||| 
| Antioxidant | Ascorbic Acid | 26 |
| Antioxidant | Sodium Metabisulfite | 74 |
| TOTAL | | 100 |

EXAMPLE 2

The hair coloring base composition and the developer composition provided below can be used with an antioxidant booster composition of Example 1, according to the methods of the instant disclosure. For example, an antioxidant booster composition of Example 1 can be combined with the hair coloring base composition and the developer composition to form an antioxidant-enriched hair coloring composition. One part of hair coloring base composition can be combined with 1 part of developer composition.

| Hair Coloring Base Composition |||
| --- | --- | --- |
| Component | Ingredients | Wt. % |
| Alkalizing agents | Ammonium Hydroxide and/or Ammonium Acetate | 11 |
| Colorants | Oxidative Dye Precursors/Couplers | 0.8 |
| Fatty Acid(s)/Fatty Alcohol(s) | Oleic Acid and/or Oleyl Alcohol | 8 |
| Surfactants/ Conditioning Agents/ Emollients | Polyglyceryl-2 Oleyl Ether, Polyglyceryl-4 Oleyl Ether, PEG-2 Oleamine, Sodium Diethylaminopropyl Cocoaspartamide, and/or Trideceth-2 Carboxamide MEA | 34 |
| Antioxidant | Erthorbic Acid | 0.2 |
| Solvents | Alcohol (denat.), Hexylene Glycol, and/or Propylene Glycol | 5 |
| Miscellaneous | Preservative(s), Chelating Agent(s), Fragrance(s), etc. | <3 |
| Water | Water | q.s. 100% |

| Developer Composition |||
| --- | --- | --- |
| Component | Ingredients | Wt. % |
| Oxidizing Agent | Hydrogen Peroxide | 12 |
| Surfactants | Cetearyl Alcohol, Ceteareth-25, and/or Trideceth-2 Carboxamide MEA | 3.8 |
| Solvent | Glycerin | 0.5 |
| Buffering Agents | Tetrasodium Pyrophosphate | <0.1 |

Developer Composition

| Component | Ingredients | Wt. % |
|---|---|---|
| Stabilizer | Tetrasodium Etidronate and/or Sodium Stannate | <1 |
| Chelating Agent | Pentasodium Pentetate and/or Sodium Salicylate | <1 |
| Water | Water | q.s. 100% |

EXAMPLE 3

The hair coloring base composition and the developer composition provided below can be used with an antioxidant booster composition of Example 1, according to the methods of the instant disclosure. For example, an antioxidant booster composition of Example 1 can be combined with the hair coloring base composition and the developer composition to form an antioxidant-enriched hair coloring composition. One part of hair coloring base composition can be combined with 1.5 parts of developer composition.

Hair Coloring Base Composition

| Component | Ingredients | Wt. % |
|---|---|---|
| Alkalizing Agents | Ammonium Hydroxide and/or Ethanolamine | 12.3 |
| Colorants | Oxidative Dye Precursors/Couplers | 1.5 |
| Fatty Acid(s)/Fatty Alcohol(s) | Lauric Acid and/or Cetearyl Alcohol | 14.5 |
| Surfactants/ Conditioning Agents/ Emollients | Laureth-12, Glycol Distearate, Oleth-30, Deceth-3, and/or Silica Dimethyl Silylate, | 24.2 |
| Cationic Polymers | Hexadimethrine Chloride and/or Polyquaternium-22 | 8.7 |
| Thickening Agent | Carbomer | 0.4 |
| Antioxidant | Ascorbic Acid | 0.25 |
| Amino Acids | Proline and/or Threonine | 1 |
| Solvent | Propylene Glycol | 10 |
| Miscellaneous | Preservative(s), Chelating Agent(s), Fragrance(s), etc. | <3 |
| Water | Water | q.s. 100% |

Developer Composition

| Component | Ingredients | Wt. % |
|---|---|---|
| Oxidizing Agent | Hydrogen Peroxide | 12 |
| Surfactants | Cetearyl Alcohol, Ceteareth-25, and/or Trideceth-2 Carboxamide MEA | 3.8 |
| Solvent | Glycerin | 0.5 |
| Buffering Agents | Tetrasodium Pyrophosphate | <0.1 |
| Stabilizer | Tetrasodium Etidronate and/or Sodium Stannate | <1 |
| Chelating Agent | Pentasodium Pentetate and/or Sodium Salicylate | <1 |
| Water | Water | q.s. 100% |

EXAMPLE 4

The hair coloring base composition and the developer composition provided below can be used with an antioxidant booster composition of Example 1, according to the methods of the instant disclosure. For example, an antioxidant booster composition of Example 1 can be combined with the hair coloring base composition and the developer composition to form an antioxidant-enriched hair coloring composition. One part of hair coloring base composition can be combined with 1.5 parts of developer composition.

Hair Coloring Base Composition

| Component | Ingredients | Wt. % |
|---|---|---|
| Alkalizing Agent | Ammonium Hydroxide and/or Ethanolamine | 10.7 |
| Reducing Agent | Ammonium Thiolactate | 0.8 |
| Colorants | Oxidative Dye Precursor/Couplers | 0.6 |
| Fatty Alcohol | Oleyl Alcohol | 1.1 |
| Surfactants/ Conditioning Agents/ Emollients | PEG-4 Rapeseedamide, Deceth-3, Glyceryl Lauryl Ether, and/or Laureth-5 Carboxylic Acid | 28.5 |
| Polymer | Poloxamer 338 | 2 |
| Cationic Polymer | Polyquaternium-6 | 3.4 |
| Antioxidant | Erythorbic Acid | 0.1 |
| Solvent | Alcohol (Denat.), Propylene Glycol, Hexylene Glycol, and/or Dipropylene Glycol | 21 |
| Miscellaneous | Preservative(s), Chelating Agent(s), Fragrance(s), etc. | <3 |
| Water | Water | q.s. 100% |

Developer Composition

| Component | Ingredients | Wt. % |
|---|---|---|
| Oxidizing Agent | Hydrogen Peroxide | 12 |
| Surfactants | Cetearyl Alcohol, Ceteareth-25, and/or Trideceth-2 Carboxamide MEA | 3.8 |
| Solvent | Glycerin | 0.5 |
| Buffering Agents | Tetrasodium Pyrophosphate | <0.1 |
| Stabilizer | Tetrasodium Etidronate and/or Sodium Stannate | <1 |
| Chelating Agent | Pentasodium Pentetate and/or Sodium Salicylate | <1 |
| Water | Water | q.s. 100% |

EXAMPLE 5

The hair coloring base composition and the developer composition provided below can be used with an antioxidant booster composition of Example 1, according to the methods of the instant disclosure. For example, an antioxidant booster composition of Example 1 can be combined with the hair coloring base composition and the developer composition to form an antioxidant-enriched hair coloring composition. One part of hair coloring base composition can be combined with 1.5 parts of developer composition.

| Hair Coloring Base Composition | | Wt. % |
|---|---|---|
| Alkalizing Agents | Ammonium Hydroxide and/or Ethanolamine | 9 |
| Colorants | Oxidative Dye Precursors/Couplers | 1.4 |
| Coupler | Resorcinol | 0.7 |
| Couplers | M-Aminophenol and/or 2,4-Diaminophenoxyethanol HCl | 0.1 |
| Fatty Alcohols | Cetearyl Alcohol | 8.8 |
| Surfactants | Steareth-2 and/or Steareth-20 | 4.2 |
| Oils | Mineral Oil and/or *Camellia Oleifera* Seed Oil | 9 |
| Cationic Polymer | Polyquaternium-6 | 1.8 |
| Antioxidant | Erythorbic Acid | 0.3 |

-continued

| Hair Coloring Base Composition | | Wt. % |
|---|---|---|
| Miscellaneous | Preservative(s), Chelating Agent(s), Fragrance(s), etc. | <3 |
| Water | Water | q.s. 100% |

| Developer Composition | | |
|---|---|---|
| Component | Ingredient(s) | Wt. % |
| Oxidizing Agent | Hydrogen Peroxide | 12 |
| Surfactants | Cetearyl Alcohol, Ceteareth-25, and/or Trideceth-2 Carboxamide MEA | 3.8 |
| Solvent | Glycerin | 0.5 |
| Buffering Agents | Tetrasodium Pyrophosphate | <0.1 |
| Stabilizer | Tetrasodium Etidronate and/or Sodium Stannate | <1 |
| Chelating Agent | Pentasodium Pentetate and/or Sodium Salicylate | <1 |
| Water | Water | q.s. 100% |

EXAMPLE 6

The hair coloring base composition and the developer composition provided below can be used with an antioxidant booster composition of Example 1, according to the methods of the instant disclosure. For example, an antioxidant booster composition of Example 1 can be combined with the hair coloring base composition and the developer composition to form an antioxidant-enriched hair coloring composition. One part of hair coloring base composition can be combined with 1 part of developer composition.

| Hair Coloring Base Composition | | |
|---|---|---|
| Component | Ingredients | Wt. % |
| Alkalizing Agent | Ethanolamine | 4.4 |
| Colorants | Oxidative Dye Precursor/Couplers | 1.3 |
| Surfactants/ Conditioning Agents/ Emollients | PEG-40 Hydrogenated Castor Oil, Sodium Lauryl Sulfate, Disodium Cocoamphodiacetate, and/or Decyl Glucoside | 8.2 |
| Thickening Agent | Hydroxypropyl Guar | 0.3 |
| Antioxidant | Ascorbic Acid | 0.1 |
| Oil | Mineral Oil, *Helianthus Anuus* (Sunflower) Seed Oil, *Camellia Oleifera* Seed Oil, and/or *Limnanthes Alba* (Meadowfoam) Seed Oil | 60.4 |
| Miscellaneous | Preservative(s), Chelating Agent(s), Fragrance(s), etc. | <3 |
| Water | Water | q.s. 100% |

| Developer Composition | | |
|---|---|---|
| Component | Ingredient(s) | Wt. % |
| Oxidizing Agent | Hydrogen Peroxide | 12 |
| Surfactants/ Conditioning Agents/ Emollients | Cetearyl Alcohol, Steareth-20, and/or PEG-4 Rapeseedamide | 12.3 |
| Oil | Mineral Oil | 20 |
| Solvent | Glycerin | 0.5 |
| Antioxidant | Tocopherol | 0.1 |

| Developer Composition | | |
|---|---|---|
| Component | Ingredient(s) | Wt. % |
| Cationic Polymers | Polyquaternium-6 and/or Hexadimethrine Chloride | 0.8 |
| Buffering Agent | Tetrasodium Pyrophosphate | <0.1 |
| Stabilizer | Tetrasodium Etidronate and/or Sodium Stannate | <1 |
| Chelating Agent | Pentasodium Pentetate and/or Sodium Salicylate | <1 |
| Water | Water | q.s. 100% |

EXAMPLE 7

Evaluation of Color Fade (ΔE)

Testing was carried out to determine the role of antioxidants on the speed and degree of color fading in artificially colored hair. A series of hair coloring compositions were prepared by combining antioxidant booster compositions A-D (shown in the table below) with 10 grams of coloring base composition and 10 grams of 20V developer composition to derive antioxidant enriched coloring compositions A-D.

| Antioxidants | A | B | C | D | E |
|---|---|---|---|---|---|
| Percent Total of AA/SS | 100%/ 100% | 100%/ 50% | 50%/ 100% | 50%/ 50% | 25%/ 25% |
| Ascorbic Acid (AA) | 0.5 | 0.5 | 0.25 | 0.25 | 0.125 |
| Sodium Sulfite (SS) | 0.5 | 0.25 | 0.5 | 0.25 | 0.125 |

Antioxidant enriched coloring compositions A-E were applied to 90% grey hair swatches and allowed to process for 35 minutes. After 35 minutes, the swatches were shampooed multiple times and the L*a*b* values were measured to determine the ΔE. The higher the ΔE, the greater degree of color change (more color fading). The hair swatches were shampooed a total of 14 times and the ΔE was determined after 3 washes, 7 washes, and 14 washes. The ΔE values are graphically presented in FIG. 1.

As shown in FIG. 1, coloring composition A having the highest amount of antioxidants (100%) showed the least color fading (the lowest ΔE). The difference in color fading became more pronounced as the number of shampooing cycles increased, i.e., the difference after 14 washes was the most pronounced. This is surprising considering that it was not known that the amount of antioxidants in coloring compositions at the time of coloring hair influenced color fading.

EXAMPLE 8

Evaluation of Color Fade (ΔE)

Testing was carried out to determine how "adding-back" antioxidants to hair coloring compositions influenced color fading in artificially colored hair. Antioxidants were added-back to hair coloring compositions that originally included antioxidants but at least a portion of the original antioxidants had degraded over time.

The same hair coloring base composition used in Example 7 was used in the instant testing. Antioxidant booster composition E of Example 4 (containing 0.125 wt. % of AA and 0.125 wt. % SS) was added into the hair coloring base composition and the hair coloring base composition was subjected to heat (45° C.) for 1 month, to force degradation of at least a portion of the antioxidants. After the hair coloring base composition had been incubated at 45° C. for 1 month, antioxidant booster composition A was combined with 10 grams of the aged coloring base composition and 10 grams of 20V developer composition to derive antioxidant enriched bleaching composition A*.

Figure 2:
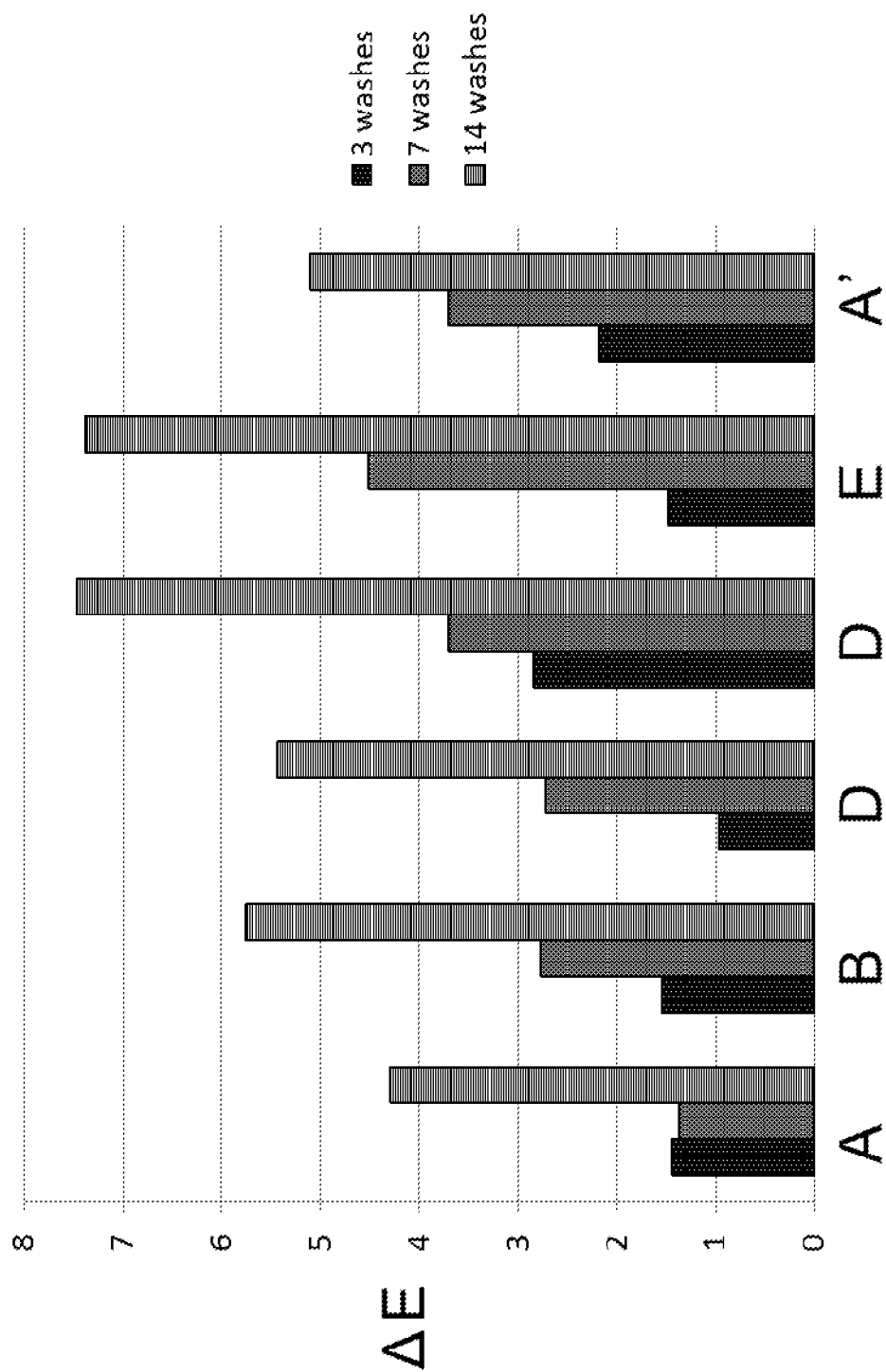
FIG. 2 is a graph showing the color fading of hair swatches treated with coloring compositions containing different amount s of antioxidants added at the time of coloring and swatches treated with an aged coloring composition in which in which antioxidants had originally been added.

Antioxidant enriched coloring compositions A* was applied to 90% grey hair swatches and allowed to process for 35 minutes. After 35 minutes, the swatches were shampooed multiple times and the L*a*b* values were measured to determine the ΔE. The resulting ΔE of the swatches treated with antioxidant enriched coloring composition A* was compared with the ΔE of the swatches treated with antioxidant enriched coloring compositions A-D of Example 7. The results are graphically presented in FIG. 2. As shown in FIG. 2, "adding back" antioxidants to derive coloring composition A* resulted in a dramatic improvement in color fading (less color fading). In other words, adding back antioxidants to compensate or supplement for the loss of antioxidants originally present in a hair coloring base composition dramatically improved coloring fading (less color fading) in artificially colored hair. This is surprising considering that it was not known that the amount of antioxidants in coloring compositions at the time of coloring hair influenced color fading of color in artificially hair.

EXAMPLE 9

Evaluation of Color Fade (ΔE)

Figure 3:
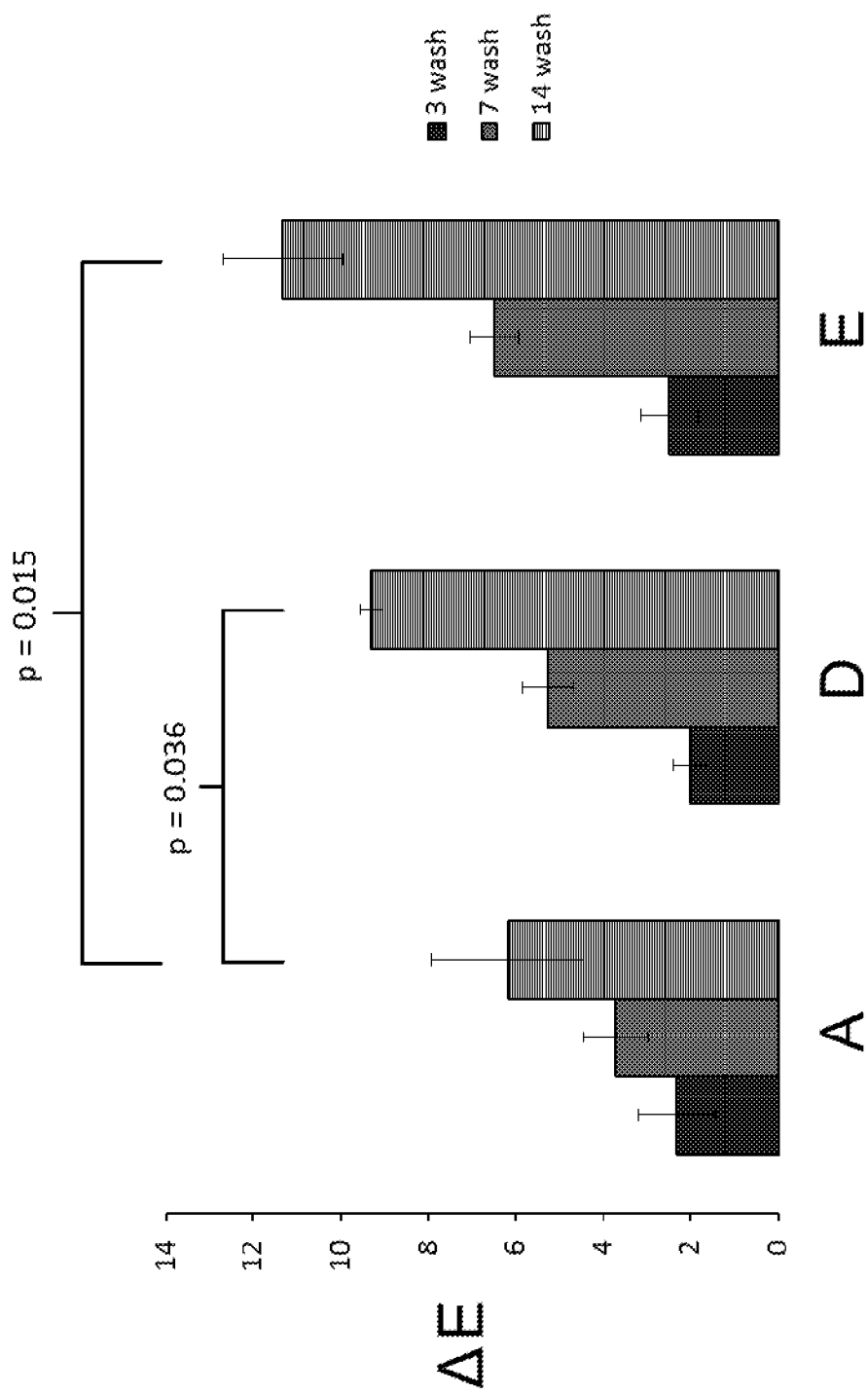
FIG. 3 is a graph showing the statistical difference in color fading of hair swatches treated with coloring compositions containing different amount of antioxidants added at the time of coloring.

To confirm statistical significance of the results of Examples 7 and 8, additional testing was carried out in triplicate. Antioxidant enriched bleaching compositions were prepared by combining the antioxidant booster compositions A, D, and E of Example 7 with 10 grams of coloring base composition and 10 grams of 20V developer composition. The resulting antioxidant enriched bleaching compositions were applied to 90% grey hair swatches and allowed to process for 35 minutes. After 35 minutes, the swatches were shampooed multiple times and the L*a*b* values were measured to determine the ΔE. The results are presented in FIG. 3. The data confirmed a statistically significant difference between ΔE values that correlated with increasing amounts of antioxidants in the hair coloring compositions. This is surprising considering that it was not known that the amount of antioxidants in coloring compositions at the time of coloring hair influenced color fading of color in artificially hair.

EXAMPLE 10

Evaluation of Color Retention

Testing was carried out to determine how antioxidants influence color retention in artificially colored hair. Antioxidants were added to commercial hair coloring products that originally included antioxidants but at least a portion of the original antioxidants had degraded over time. Antioxidant booster compositions were added into four different commercial hair coloring base compositions that had been aged for 2 months, 6 months, or 51 months. Antioxidant booster compositions were also added into a commercial hair coloring composition that was not aged (fresh).

0.6 grams of ascorbic acid or 0.85 grams of a mixture of 33% ascorbic acid, 33% erythorbic acid, and 33% sodium sulfite was added to 56 mL of aged commercial hair coloring base composition. 3.5 grams of a direct dye booster composition, which is sold together in the kit of the commercial product, was also added. 84 mL of developer (25V) was added to provide an antioxidant enriched hair coloring composition. The antioxidant enriched hair coloring composition was applied to 90% grey hair swatches and allowed to process for 25 minutes. The hair was subjected to initial L*a*b* analysis. The swatches were then shampooed fifteen times and the L*a*b* values were again measured to determine the percent color retention, which was compared with 90% grey hair swatches that had been colored using the same commercial hair coloring product without the addition of the antioxidant booster composition. The ΔE values were used to determine the percent retention of color according to the below formula:

$$\% \text{ Color Retention} = \left( \frac{[\text{Initial Color Deposition}] - [\text{Color Shift}]}{[\text{Initial Color Deposition}]} \right) \times 100$$

The results are presented in the table below.

| | Commercial Product #1 (Violet - Mix/Hair Ratio of 3:1) | | |
|---|---|---|---|
| | Age 2 months Added Antioxidants | | |
| | None* | 0.6 g (100% ascorbic acid) | 0.85 g (33% ascorbic acid, 33% erythorbic acid, and 33% sodium sulfite) |
| ΔE$_{Initial}$ | 45.6 | 45.7 | 45.5 |
| ΔE$_{+15\ Washes}$ | 37.8 | 39.0 | 38.4 |
| % Retention | 82.8 | 85.2 | 84.2 |

*Included whatever antioxidants existed in the original product but no additional antioxidants were added.

0.6 grams of ascorbic acid or 0.85 grams of a mixture of 33% ascorbic acid, 33% erythorbic acid, and 33% sodium sulfite was added to 50 mL of aged commercial hair coloring base composition. 75 mL of developer (20V) was then added to provide an antioxidant enriched hair coloring composition. The antioxidant enriched hair coloring composition was applied to 90% grey hair swatches and allowed to process for 35 minutes. The hair was subjected to initial L*a*b* analysis. The swatches were then shampooed fifteen times and the L*a*b* values were again measured to determine the percent color retention, which was compared with 90% grey hair swatches that had been colored using the same commercial hair coloring product but did not include the antioxidant booster composition. The ΔE values were used to determine the percent color retention. The results are presented in the table below.

Commercial Product #2
(Red - Mix/Hair Ratio of 3:1)

| | Age |||
|---|---|---|---|
| | 51 months |||
| | Added Antioxidants |||
| | None* | 0.6 g (100% ascorbic acid) | 0.85 g (33% ascorbic acid, 33% erythorbic acid, and 33% sodium sulfite) |
| $\Delta E_{Initial}$ | 42.8 | 42.5 | 42.0 |
| $\Delta E_{+15\ Washes}$ | 36.1 | 37.2 | 36.8 |
| % Retention | 84.3 | 87.6 | 87.5 |

*Included whatever antioxidants existed in the original product but no additional antioxidants were added.

0.6 grams of ascorbic acid was added to 50 mL of aged commercial hair coloring base composition. 75 mL of developer (20V) was then added to provide an antioxidant enriched hair coloring composition. The antioxidant enriched hair coloring composition was applied to 90% grey hair swatches and allowed to process for 35 minutes. The hair was subjected to initial L*a*b* analysis. The swatches were then shampooed fifteen times and the L*a*b* values were again measured to determine the percent color retention, which was compared with 90% grey hair swatches that had been colored using the same commercial hair coloring product that did not include the antioxidant booster composition. The ΔE values were used to determine the percent color retention. The results are presented in the table below.

Commercial Product #3
(Red - Mix/Hair Ratio of 5:1)

| | Age ||
|---|---|---|
| | 51 months ||
| | Added Antioxidants ||
| | None* | 0.6 g (100% ascorbic acid) |
| $\Delta E_{Initial}$ | 39.0 | 39.4 |
| $\Delta E_{+15\ Washes}$ | 30.3 | 33.5 |
| % Retention | 68.5 | 81.9 |

*Included whatever antioxidants existed in the original product but no additional antioxidants were added.

0.6 grams of ascorbic acid was added to 56 mL of aged commercial hair coloring base composition. 3.5 grams of a direct dye booster composition, which is sold together in the kit of the commercial product, was also added. 84 mL of developer (25V) was added to provide an antioxidant enriched hair coloring composition. The antioxidant enriched hair coloring composition was applied to 90% grey hair swatches and allowed to process for 25 minutes. The hair was subjected to initial L*a*b* analysis. The swatches were then shampooed fifteen times and the L*a*b* values were again measured to determine the percent color retention, which was compared with 90% grey hair swatches that had been colored using the same commercial hair coloring product that did not include the antioxidant booster composition. The ΔE values were used to determine the percent retention. The results are presented in the table below.

Commercial Product #4
(Violet - Mix/Hair Ratio of 5:1)

| | Age ||
|---|---|---|
| | 6 months ||
| | Added Antioxidants ||
| | None* | 0.6 g (100% ascorbic acid) |
| $\Delta E_{Initial}$ | 43.8 | 43.5 |
| $\Delta E_{+15\ Washes}$ | 36.7 | 38.2 |
| % Retention | 83.7 | 88.0 |

*Included whatever antioxidants existed in the original product but no additional antioxidants were added.

0.6 grams of ascorbic acid was added to 56 mL of fresh commercial hair coloring base composition. 3.5 grams of a direct dye booster composition, which is sold together in the kit of the commercial product, was also added. 84 mL of developer (25V) was added to provide an antioxidant enriched hair coloring composition. The antioxidant enriched hair coloring composition was applied to 90% grey hair swatches and allowed to process for 25 minutes. The hair was subjected to initial L*a*b* analysis. The swatches were then shampooed fifteen times and the L*a*b* values were again measured to determine the percent color retention, which was compared with 90% grey hair swatches that had been colored using the same commercial hair coloring product that did not include the antioxidant booster composition. The ΔE values were used to determine the percent color retention. The results are presented in the table below.

Commercial Product #5
(Red - Mix/Hair Ratio of 5:1)

| | Age ||
|---|---|---|
| | Fresh ||
| | Added Antioxidants ||
| | None* | 0.6 g (100% ascorbic acid) |
| $\Delta E_{Initial}$ | 49.6 | 50.0 |
| $\Delta E_{+15\ Washes}$ | 42.9 | 44.6 |
| % Retention | 80.4 | 82.5 |

*Included whatever antioxidants existed in the original product but no additional antioxidants were added.

As shown by the data in the tables above, use of an antioxidant booster composition surprisingly improved the percent color retention for all commercial hair coloring products, for all time periods measured (fresh, 2 months, 6 months, and 51 months), and for all antioxidants tested (ascorbic acid, erythorbic acid, and sodium sulfite).

EXAMPLE 11

(Evaluation of Color Fade (ΔE))

Additional testing was carried out to determine how antioxidants influenced color fading in artificially colored hair. Antioxidants were added to a commercial hair coloring product that originally included antioxidants but at least a portion of the original antioxidants had degraded over time. Different combinations of antioxidant booster compositions were added into commercial hair coloring base compositions that had been aged for 2 months. 3 grams of an antioxidant booster composition was added to 45 mL of a hair coloring base composition. The hair coloring base composition was combined with 67.5 mL of developer (20V) to derive an antioxidant enriched hair coloring composition. The antioxidant enriched hair coloring composition was applied to 90% grey permed hair and to 90% grey un-permed hair and allowed to process for 30 minutes. The hair was subjected to initial L*a*b* analysis. The swatches were then shampooed 5, 10, and 15 times and the L*a*b* values were measured at each interval. The results are compared to hair swatches that were colored using the same commercial hair coloring products without the addition of an antioxidant booster composition (standard). The ΔE values are presented in the table below.

| ΔE for Permed Hair Commercial Product #6 - Light Intense Auburn) | | | |
| --- | --- | --- | --- |
| | ΔE 5 Washes | ΔE 10 Washes | ΔE 15 Washes |
| Standard | 3.7 | 7.3 | 9.4 |
| Vitamin C | 2.1 | 3.8 | 5.1 |
| Vitamin E & Vitamin C (50%:50%) | 4.2 | 5.9 | 8.4 |
| Selenium Sulfide & Vitamin E (50%:50%) | 4.6 | 7.4 | 9.6 |
| Vitamin C, Selenium Sulfide, & Vitamin E (33%:33%:33%) | 3.6 | 6.6 | 9.5 |

| ΔE for Un-Permed Hair Commercial Product #6 - Light Intense Auburn) | | | |
| --- | --- | --- | --- |
| | ΔE 5 Washes | ΔE 10 Washes | ΔE 15 Washes |
| Standard | 1.8 | 4.3 | 4.7 |
| Vitamin C | 0.9 | 1.5 | 2.1 |
| Vitamin E & Vitamin C (50%:50%) | 1.5 | 3.7 | 3.5 |
| Selenium Sulfide & Vitamin E (50%:50%) | 2.8 | 3.5 | 5.1 |
| Vitamin C, Selenium Sulfide, & Vitamin E (33%:33%:33%) | 0.7 | 2.4 | 3.0 |

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

All percentages, parts and ratios herein are based upon the total weight of the compositions of the present invention, unless otherwise indicated.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or the fatty compound (the single fatty acid does not serve as both the emulsifier and the fatty component).

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat" (and its grammatical variations) as used herein also refers to contacting keratinous substrates such as hair with the compositions of the present disclosure.

A "rinse-off" product refers to a composition that is rinsed and/or washed from the hair with water either after or during the application of the composition onto the hair, and before drying and/or styling the hair. At least a portion of the composition is removed from the hair during the rinsing and/or washing.

A "leave-on" product refers to a composition that is not rinsed and/or washed from the hair after or during application of the composition onto the hair. The composition remains on the hair during drying and/or styling.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A method for coloring hair and improving the durability of the color, the method comprising:
    (I) combining an antioxidant booster composition, a hair coloring base composition, and a developer composition to form an antioxidant-enriched hair coloring composition within 2 hours of application to the hair, wherein the antioxidant-enriched hair coloring composition is free of pyrazolones;
    (II) applying the antioxidant enriched hair coloring composition to the hair and allowing the antioxidant enriched hair coloring composition to remain on the hair for a period of time; and
    (III) rinsing the antioxidant enriched hair coloring composition from the hair; wherein,
        (a) the antioxidant booster composition comprises:
            (i) one or more antioxidants, wherein the one or more antioxidants comprises ascorbic acid;
        (b) the hair coloring base composition comprises:
            (i) one or more oxidative dye precursors; and
            (ii) one or more alkalizing agents;
        (c) the developer composition comprises:
            (i) one or more oxidizing agents; and
            (ii) a cosmetically acceptable carrier.

2. The method of claim 1, wherein the hair coloring base composition and the developer composition are combined with each other before combination with the antioxidant booster composition.

3. The method of claim 1, wherein the antioxidant booster composition comprises one or more antioxidants selected from the group consisting of sodium sulfite, sodium metabisulfite, sodium hydrosulfite, tocopherols, alpha-tocopherol, tocopheryl acetate, panthenol, selenium sulfide, zinc formosulfoxylate, erythorbic acid, isoascorbic acid, thioglycolate salt, magnesium ascorbyl phosphate, ascorbyl glucoside, cysteine, thiourea, thiolactic acid, glyceryl monothioglycolate, thioglycerol, 2,5-dihydroxybenzoic acid, and a mixture thereof.

4. The method of claim 1, wherein the antioxidant booster composition further comprises:
    (ii) one or more fillers and/or carriers.

5. The method of claim 4, wherein
    the antioxidant booster composition is in powder form and comprises one or more fillers selected from the group consisting of starches, maltodextrins, calcium silicates, perlites, zeolites, polylactic acids, silicas, polyamide powders, polyvinylpyrrolidones, dextrose, oligosaccharides, celluloses, diatomite, diatomaceous earth, talc, magnesium silicates, clays, vitamin powders, amino acid powders and their derivatives, silicon dioxide, and a mixture thereof; or
    the antioxidant booster composition is in liquid form and comprises one or more carriers selected from the group consisting of water, organic solvents, natural oils, synthetic oils, ester oils, hydrocarbons, silicones, and a mixture thereof.

6. The method of claim 1, wherein the hair coloring base composition comprises one or more alkalizing agents selected from the group consisting of ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol, guanidium salts, alkali metal hydroxides, sodium hydroxide, alkali metal carbonates, and a mixture thereof.

7. The method of claim 1, wherein the antioxidant booster composition further comprises:
    (iii) one or more conditioning agents.

8. The method of claim 1, wherein the hair coloring base composition comprises about 1 to about 20 wt. % of the one or more alkalizing agents, based on the total weight of the hair coloring base composition.

9. The method of claim 1, wherein the hair coloring base composition comprises one or more oxidative dye precursors selected from the group consisting of ortho- and/or para-aminophenols, ortho- and/or para-phenylenediamines, double bases, heterocyclic bases, acid addition salts thereof, and a mixture thereof.

10. The method of claim 1, wherein the hair coloring base composition comprises about 0.01 to about 10 wt. % of the one or more hair oxidative dye precursors.

11. The method of claim 1, wherein the developer composition comprises one or more oxidizing agents selected from the group consisting of hydrogen peroxide, inorganic alkali metal peroxides as sodium periodate and sodium peroxide, organic peroxides, urea peroxide, melamine peroxide, inorganic perhydrate salts, alkali metal salts of perborates, percarbonates, perphosphates, persilicates, and persulphates, bromates, and a mixture thereof.

12. The method of claim 11, wherein the one or more oxidizing agents comprises hydrogen peroxide.

13. The method of claim 1, wherein the developer composition comprises about 0.5 to about 40 wt. % of the one or more oxidizing agents, based on the total weight of the developer composition.

14. The method of claim 1, wherein the developer composition comprises a cosmetically acceptable carrier selected from the group consisting of water, water-soluble solvents, organic solvents, natural oils, synthetic oils, esters, hydrocarbons, silicones, and a mixture thereof.

15. The method of claim 1, wherein the developer composition is essentially anhydrous.

16. The method of claim 1, wherein the developer composition comprises about 40 to about 98 wt. % of the cosmetically acceptable carrier.

17. The method of claim 2 wherein the hair coloring base composition and the developer composition are combined in a ratio of about 1:1 to about 1:5 (hair coloring base composition:developer).

18. The method of claim 1, wherein the antioxidant-enriched coloring composition comprises about 0.01 to about 2 wt. % of total antioxidants, based on the total weight of the antioxidant-enriched coloring composition.

19. A kit comprising:
(a) an antioxidant booster composition comprising:
   (i) one or more antioxidants, the one or more antioxidants comprises ascorbic acid; and
(b) a hair coloring base composition comprising:
   (i) one or more oxidative dye precursors; and
   (ii) one or more alkalizing agents;
      wherein the antioxidant booster composition and the hair coloring base composition are separately contained.

20. The kit of claim 19, further comprising:
(c) a developer composition comprising:
   (i) one or more oxidizing agents; and
   (ii) a cosmetically acceptable carrier;
   wherein the antioxidant booster composition, the hair coloring base composition, and the developer composition are separately contained.

21. The method of claim 3, wherein the antioxidant booster composition comprises at least one of erythorbic acid and sodium sulfite.

* * * * *